US009510951B2

(12) United States Patent
Bachmaier (10) Patent No.: US 9,510,951 B2
(45) Date of Patent: Dec. 6, 2016

(54) STEMLESS SHOULDER IMPLANT

(71) Applicant: Arthrex, Inc., Naples, FL (US)

(72) Inventor: Samuel Bachmaier, Mauern (DE)

(73) Assignee: ARTHREX, INC., Naples, FL (US)

( * ) Notice: Subject to any disclaimer, the term of this patent is extended or adjusted under 35 U.S.C. 154(b) by 0 days.

(21) Appl. No.: 13/936,946

(22) Filed: Jul. 8, 2013

(65) Prior Publication Data
US 2014/0379089 A1    Dec. 25, 2014

(30) Foreign Application Priority Data

Jun. 19, 2013    (EP) ..................................... 13172917

(51) Int. Cl.
*A61F 2/30*    (2006.01)
*A61F 2/40*    (2006.01)

(52) U.S. Cl.
CPC ........... *A61F 2/4014* (2013.01); *A61F 2/4003* (2013.01); *A61F 2002/30332* (2013.01); *A61F 2002/30433* (2013.01); *A61F 2002/30571* (2013.01); *A61F 2002/30579* (2013.01); *A61F 2002/30784* (2013.01); *A61F 2002/30822* (2013.01); *A61F 2002/30881* (2013.01);
(Continued)

(58) Field of Classification Search
CPC ...... A61F 2/3601; A61F 2/4003; A61F 2/40; A61F 2002/30329; A61F 2002/30331; A61F 2002/30484; A61F 2002/30579; A61F 2002/30594; A61F 2002/303604; A61F 2002/30611; A61F 2002/3605; A61F 2002/4007; A61F 2/4014; A61F 2002/30332; A61F 2002/30433; A61F 2002/30571; A61F 2002/30784; A61F 2002/30822; A61F 2002/30881; A61F 2002/4018; A61F 2002/4022

USPC ......... 623/19.11–19.14, 21.13, 22.11, 22.15, 623/22.19, 22.4, 22.41, 22.45–22.46, 23.41, 623/23.18, 23.39, 23.4, 23.42
See application file for complete search history.

(56) References Cited

U.S. PATENT DOCUMENTS

| | | | | |
|---|---|---|---|---|
| 5,108,446 | A | * | 4/1992 | Wagner ..................... A61F 2/34 623/22.26 |
| 5,702,457 | A | * | 12/1997 | Walch et al. ............... 623/19.13 |
| 7,258,699 | B2 | * | 8/2007 | Errico ..................... A61F 2/442 623/17.14 |

(Continued)

FOREIGN PATENT DOCUMENTS

| | | | |
|---|---|---|---|
| DE | 101 23 517 C1 | 11/2002 | |
| DE | 10123517 | * 11/2002 | ............... A61F 2/40 |

(Continued)

OTHER PUBLICATIONS

Translation of DE102004042502A1. Mar. 2, 2006.*

(Continued)

*Primary Examiner* — Thomas J Sweet
*Assistant Examiner* — Christie Bahena
(74) *Attorney, Agent, or Firm* — Karish & Bjorgum, PC (57) ABSTRACT

A humerus implant includes a cup shaped body and a locking adapter. The cup shaped body has a center portion and a plurality of flexible first sidewall segments and second sidewall segments, with gaps between neighbored sidewall segments. The first sidewall segments have a plurality of locking fins while the second sidewall segments having a plurality of recesses and holes. The locking adapter has means for fixing the locking adapter to the cup shaped body and a locking ring for locking the sidewall segments into their final positions.

14 Claims, 7 Drawing Sheets

(52) U.S. Cl.
CPC  *A61F2002/4018* (2013.01); *A61F 2002/4022* (2013.01)

(56) References Cited

U.S. PATENT DOCUMENTS

| | | | |
|---|---|---|---|
| 7,819,923 B2 | 10/2010 | Stone et al. | |
| 2004/0267370 A1* | 12/2004 | Ondrla | 623/19.11 |
| 2006/0217815 A1* | 9/2006 | Gibbs et al. | 623/22.17 |
| 2008/0234830 A1* | 9/2008 | Hershberger et al. | 623/22.15 |
| 2009/0143865 A1* | 6/2009 | Hassler | A61F 2/40 623/19.11 |
| 2009/0210065 A1 | 8/2009 | Nerot et al. | |
| 2009/0306782 A1 | 12/2009 | Schwyzer | |
| 2010/0049327 A1* | 2/2010 | Isch et al. | 623/19.12 |
| 2012/0016485 A1* | 1/2012 | Sharp | 623/22.21 |
| 2012/0179263 A1 | 7/2012 | Metcalfe et al. | |
| 2012/0191201 A1* | 7/2012 | Smits et al. | 623/19.11 |
| 2013/0090736 A1* | 4/2013 | Katrana et al. | 623/19.13 |
| 2013/0245775 A1* | 9/2013 | Metcalfe | 623/19.12 |
| 2013/0325130 A1* | 12/2013 | Viscardi et al. | 623/19.11 |

FOREIGN PATENT DOCUMENTS

| | | | | |
|---|---|---|---|---|
| DE | 102004042502 A1 * | 3/2006 | | A61F 2/40 |
| EP | 2 574 313 A1 | 4/2013 | | |
| FR | 2 970 411 A1 | 7/2012 | | |
| WO | WO 2007/031575 A1 | 3/2007 | | |
| WO | WO 2012/035266 A1 | 3/2012 | | |

OTHER PUBLICATIONS

Translation of DE10123517. Irlenbusch. Nov. 28, 2002.*
Translation of Hormansdorfer (DE102004042502A1) Feb. 3, 2006. Google patent translation.*

* cited by examiner

FIG. 13

STEMLESS SHOULDER IMPLANT

PRIORITY CLAIM

This application claims priority to pending European Application No. 13172917.0 filed on 19, Jun. 2013.

BACKGROUND OF THE INVENTION

1. Field of the Invention

The present invention relates to a shoulder arthroplasty system to surgical reconstitution of the shoulder and, in particular, to a humerus implant.

2. Description of Relevant Art

The shoulder joint is a ball-and-socket joint, which has an exceptional range of motion. Shoulder instability and other maladies of the shoulder joint, such as arthrosis or fracture, may require a replacement of the joint.

A shoulder joint prosthesis, which includes the replacement of the convex head of the humerus, is disclosed in U.S. Pat. No. 7,819,923. It reflects the orientation and the center of rotation of actual joints. In the case of a worn or damaged rotator cuff or too much bone loss, such prosthesis would not recover the range of motion. In such a case, a reverse shoulder prosthesis may be preferable. An example of such prosthesis is disclosed in the US patent application publication 2009/0210065 A1. In such prosthesis, the humeral component includes a stem and a cup attached to the stem. The glenoid component supports a convex head, which articulates with the cup of the humeral component. For inserting the stem into the humerus, a significant amount of bone substance has to be removed. This complicates later revision due to the low remaining bone volume.

An implant as disclosed in the US patent application publication 2009/0306782 A1 requires only a minimum of bone material to be removed. Here fixation of the implant within the bone is far less stable compared to a stem.

An improved implant is disclosed in the US patent application publication 2012/0179263 A1 by the same inventors of this application. The implant has a cup shaped body with an outer thread. The thread has a plurality of fins with cutouts between the fins. The fins have inclined leading surfaces to minimize insertion torque.

SUMMARY OF THE INVENTION

The embodiments are based on the object of providing a humerus implant which may be used as part of a shoulder prosthesis and which can be securely fixed within the humerus with minimal removal of bone material. The fixation procedure should be simple and quick. A good fixation shall be achieved immediately after insertion, without cementing, so that the joint can be used immediately after insertion. A high retention force should be achieved. A precise placement and orientation of the implant should be possible.

In an embodiment, the humerus implant has a cup shaped body having flexible sidewall segments connected together at a center portion. There may be any number of sidewall segments between 2 and 24. Preferably, six sidewall segments are provided. There are at least two different types of sidewall segments. Whereas the sidewall segments basically have the same inner contour, they differ in the outer shape, which has to provide a stable, secure and long-lasting contact with the surrounding bone. Preferably, four first sidewall segments and two second sidewall segments are provided. The different types of sidewall segments are optimized for different properties. A first type of sidewall segments preferably has a plurality of locking fins, which immediately anchor the cup shaped body within the bone. Due to the radial anchoring in the bone material, the fins cause a comparatively high pull out force of the implant. Further cementing is no more necessary. A second type of sidewall segments preferably has a structure of recesses and holes, which allow ingrowth of the bone. The recesses increase the pull out force of the cup shaped body, while the holes block rotation. Preferably, the at least two types of sidewall segments are at least partially arranged alternating. This allows for a good distribution of the properties of both kinds of sidewall segments over the circumference of the cup shaped body. To allow insertion of the cup shaped body into a bone, gaps are provided between the individual sidewall segments. Accordingly, the gaps are between neighbored segments. These allow a slight compression of the sidewall segments during insertion and therefore a reduction of the outer circumference of the cup shaped body. Due to be reduced circumference, the cup shaped body can easily be inserted into a hole of the bone.

It is further preferred, if there is at least one, preferably two tabs, close to the upper side of one or two sidewall segments and extending radially from the cup shaped body. The at least one tabs preferably are essentially parallel to plane defined by the upper ends of the sidewall segments. They allow for a precise alignment of the cup shaped body. First, the cup shaped body may be aligned, so that at least one tabs are located on the bone surface. This allows an alignment of the tilt of the cup shaped body. With implants, known from prior art, a spherical implant can be inserted into a spherical hole under any tilt angle. This may lead to a misplacement of the implant. When the at least one tabs contact the bone surface, the implant is parallel to the bone surface, without any tilt error. Therefore, the insertion alignment is improved. The at least one tabs further increase stability of the implant immediately after insertion. When the implant is correctly installed and the at least one tabs contact the bone surface, they can provide additional load bearing capacity and optional tilt moment and therefore increase the stability significantly.

Furthermore, the at least one tabs allow orientation of the implant in rotation. The implant preferably has an outer structure of the sidewall segments, which is adapted to different bone structures to optimize the fixation within the bone. Therefore, the implant may not be rotational symmetrical. To prevent a wrong insertion of the implant, the at least one tabs give an indication of the correct rotation.

After insertion of the implant into a bone, the implant must be locked. This is done by a locking adapter. For simplified insertion, the locking adapter has a conical outer contour. It may also be a tapered shank. During insertion the sidewall segments slide at the conical outer contour and are continuously pressed outwards towards the bone. This presses the locking fins into the surrounding bone. It preferably provides a locking ring, which interfaces with the sidewall segments and locks the sidewall segments into their final position with respect to the bone. Preferably, the locking ring surrounds the edges of the sidewall segments to hold them firmly in their position independent of pushing or pulling forces. The locking adapter preferably has means for holding further components, like a spherical liner. Such means may be a rotational symmetric contour into which these further components may be snapped in. It is further preferred, if the locking adapter provides a hole for a screw corresponding to a thread in the cup shaped body. By means of these components, a screw may be used to hold the locking adapter at the cup shaped body. There may be further centering means for centering the locking adapter with in the cup shaped body. Preferably, the centering means has a cylindrical shape interfacing with a cylindrical part of the center portion of the cup shaped body.

In a further embodiment, there may be a second locking adapter, which has a tapered shank for holding a spherical cap, preferably for an anatomical application, which has a corresponding conical hole. There may be a simple press fit to hold these components together. There may be further snap-in the means. There may be variations of the cap deviating from a sphere and being adapted to specific anatomical requirements According to another embodiment, the humerus implant has a cup shaped body having sidewalls between a top side and a bottom side. At the outside of the body is a thread having a plurality of fins starting with a first fin and ending with a last fin. There are cutouts between the fins. The fins are specifically designed to secure the body within the bone even without cementing. Due to the radial anchoring in the bone material, the fins cause a comparatively high pull out force of the implant. At least one fin, preferably a plurality of fins, most preferably all fins have an inclined leading surface which helps in incising the bone by rotating the body in an inward direction. By this measure, the insertion torque is minimized. The inclination of the leading surface may also be negative resulting in an undercut leading surface. There may be a combination of different types of fins in one thread. Furthermore at least one fin, preferably a plurality of fins, most preferably all fins have a forward oriented undercut trailing surface. This results in an angle of less than 90 degrees between a top surface and the trailing surface, blocking rotation in the opposite, outward direction. Therefore, the removal torque is maximized. Between the individual fins there are cutouts leaving room for abraded bone material and therefore further reducing the insertion torque and avoiding chattering. Tests have proven that this thread design results in removal torques similar to and preferably at least 60% of insertion torques immediately after insertion and without any recovery period allowing further bone growth into the structure. Due to such bone growth, the removal torque increases further with time.

It is further preferable, if the top surface is also slightly inclining. It is preferred to have approximately straight leading, top and trailing surfaces, although any one or multiple surfaces may be rounded or arc shaped, which may result in a saw tooth like design.

By filling the cutouts with cement or bone grafts or substitutes the stability may further be increased.

In a preferred embodiment at least one fin, preferably a plurality of fins, and most preferably all fins extend in a radial direction from the cup shaped body.

The humerus implant may directly interface with the glenoid component of a reverse (inverse) shoulder prosthesis. It may also be designed to hold a joint adapter to interface with the glenoid component of a reverse shoulder prosthesis. In this case, the joint adapter is inserted into the cup shaped body preferably by means of a second locking adapter. It may furthermore be designed to hold the humerus component of an anatomical prosthesis.

In another embodiment, the humerus implant is designed to provide an interface for the humeral component of an anatomical prosthesis.

In the most preferred embodiment, it is designed to provide a combination interface for a joint adapter to interface with the glenoid component of a reverse prosthesis and the humeral component of an anatomical prosthesis. Here specifically the cup shape allows a more simple and robust interface for the humeral component of an anatomical prosthesis, which for example may be held by a Morse taper. This embodiment allows simple replacement of an anatomical prosthesis by a reverse prosthesis during revision. Here exchanging of a prosthesis stem is no more necessary. Even the implant can remain in place, as only the heads must be exchanged.

The humerus implant may be manufactured from Titanium alloy, or other biocompatible metallic or non-metallic materials. The external surfaces of the device may be enhanced to allow by additive or subtractive processes, the application of texture or osteoinductive/osteoconductive material.

The humerus implant or a joint adapter may be manufactured by using Ultra High Molecular Weight Polyethylene, or other biocompatible material suitable for use as a bearing surface in concert with a mating component of complimentary geometry.

Another aspect of the invention relates to a method for inserting a humerus implant. The method includes at least the steps of resecting a portion of the humerus head, reaming or drilling a hole into the humerus head. The hole preferably having a diameter equal or slightly less than the diameter of the humerus implant with inserted locking adapter. The next step is inserting a cup shaped body with its sidewall segments pressed to each other to reduce the outer diameter of the cup shaped body. During insertion preferably at least one tab is oriented parallel to the bone surface and into a desired direction, preferably inferior. After insertion of the cup shaped body into the bone, a locking adapter is inserted into the cup shaped body, thus expanding this sidewall segments and pressing this sidewall segments towards the bone causing locking fins of the sidewall segments to penetrate into the bone. This step causes secure anchoring of the humerus implant within the bone material. The locking adapter is then fixed by a screw within the cup shaped body. In a final step, a liner or a spherical cap or any other suitable joint adapter may be attached to the locking adapter.

The present invention relates to a modular shoulder arthroplasty system to address preferably osteoarthritis, trauma and cuff tear arthropathy. The invention is not limited to such applications. It may also be used to replace any other joint.

BRIEF DESCRIPTION OF THE DRAWINGS

In the following, the invention will be described by way of example, without limitation of the general inventive concept, on examples of embodiment and with reference to the drawings.

While the invention is susceptible to various modifications and alternative forms, specific embodiments thereof are shown by way of example in the drawings and will herein be described in detail. It should be understood, however, that the drawings and detailed description thereto are not intended to limit the invention to the particular form disclosed, but on the contrary, the intention is to cover all modifications, equivalents and alternatives falling within the spirit and scope of the present invention as defined by the appended claims.

DETAILED DESCRIPTION OF THE PREFERRED EMBODIMENTS

Figure 1:
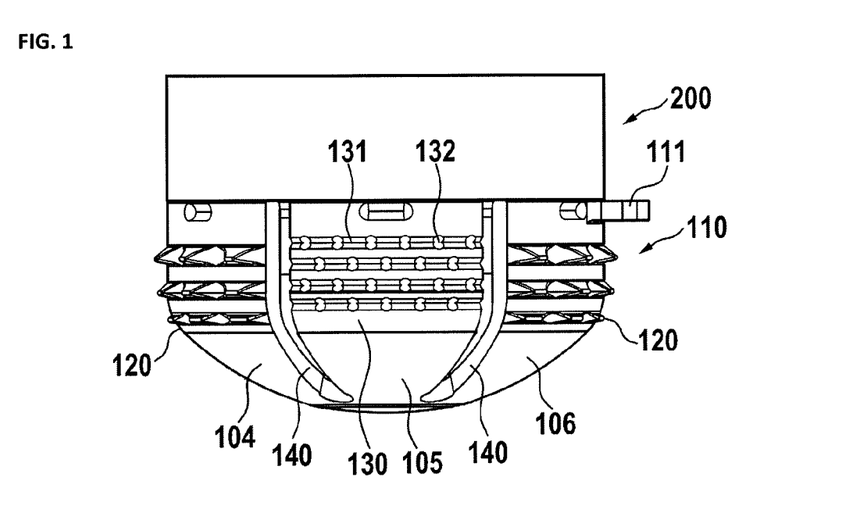
FIG. 1 shows an embodiment of a humerus implant in a side view.

FIG. 1 shows an embodiment of a humerus implant in a side view. The implant has a cup shaped body 100, which include of a plurality of sidewall segments. There are first sidewall segments 104, 106, 120 having locking fins 122. These locking fins immediately anchor the cup shaped body within the bone. Due to the radial anchoring in the bone material, the fins cause a comparatively high pull out force of the implant. Further cementing is no more necessary.

Second sidewalls 130 have recesses 131 and holes 132, which allow ingrowth of the bone. The recesses increase the pull out force of the cup shaped body, while the holes block rotation. Preferably, there are gaps 140 between the sidewall segments, which allow a compression of the sidewall segments during insertion and therefore a reduction of the outer circumference of the cup shaped body. Due to be reduced circumference, the cup shaped body can easily be inserted into a hole of the bone. At least one tab 111 is provided for alignment and for increasing tilt moment of the cup shaped body as described above in detail. On the top of the cup shaped body 100 is a locking adapter 200.

Figure 2:
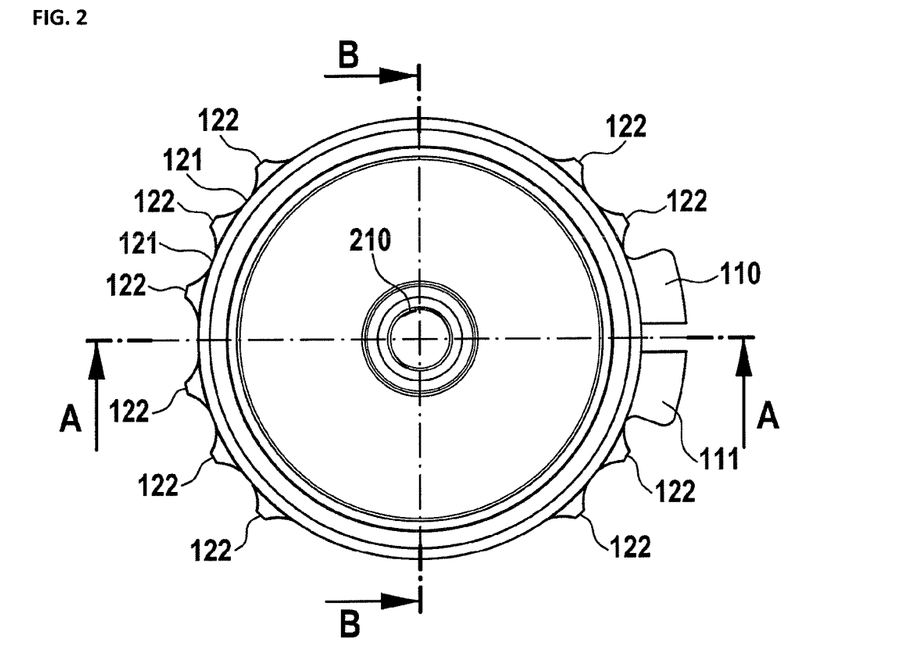
FIG. 2 shows an embodiment of a humerus implant in a top view.

FIG. 2 shows an embodiment of a humerus implant in a top view. Here, the locking fins 122 and the gaps 121 in between the fins can be seen. A screw can be inserted into hole 210 to lock the locking adapter 200 against the cup shaped body 100. Furthermore, this figure shows an arrangement symmetrically to sectional line A-A with two tabs 110, 111.

Figure 3:
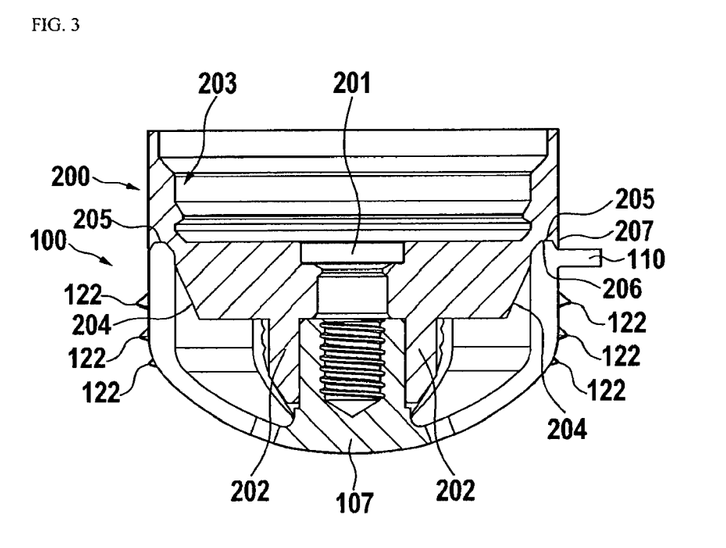
FIG. 3 shows a first sectional view.

FIG. 3 shows a first sectional view at the sectional line A-A of FIG. 2. The center portion 107 is connecting the sidewall segments. The locking adapter 200 has a hole for screw 201 and centering means 202, which preferably interface with a cylindrical component of the center portion 107. Furthermore, a conical contour is provided to simplify insertion of the locking adapter into the cup shaped body, pushing the sidewall segments to the outside until they are locked by a locking ring 205. The locking ring surrounds the edges of the sidewall segments to hold them firmly in their position independent of pushing or pulling forces. The locking ring may furthermore have means 203 for holding further components. Such components may be snapped into such a means.

Figure 4:
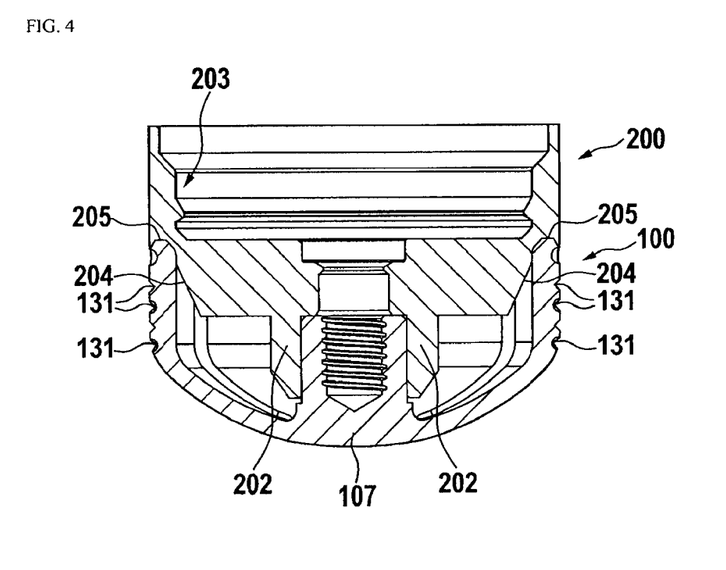
FIG. 4 shows a second sectional view.

FIG. 4 shows a second sectional view at sectional line B-B. Here, the recesses 131 instead of the locking fins of the previous figure at the outside of the sidewall segments are shown.

Figure 5:
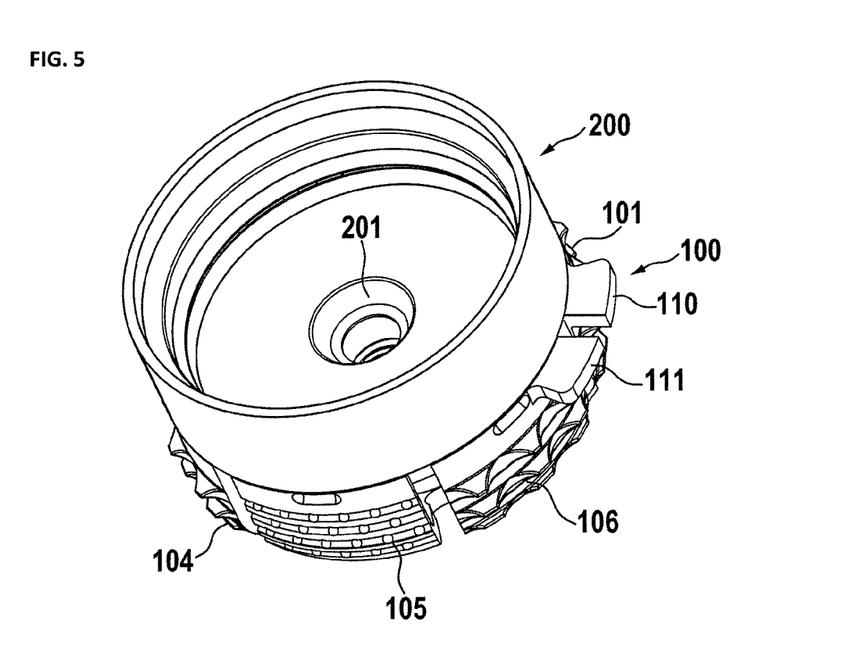
FIG. 5 shows a perspective view to the top side.

FIG. 5 shows a perspective view to the top side.

Figure 6:
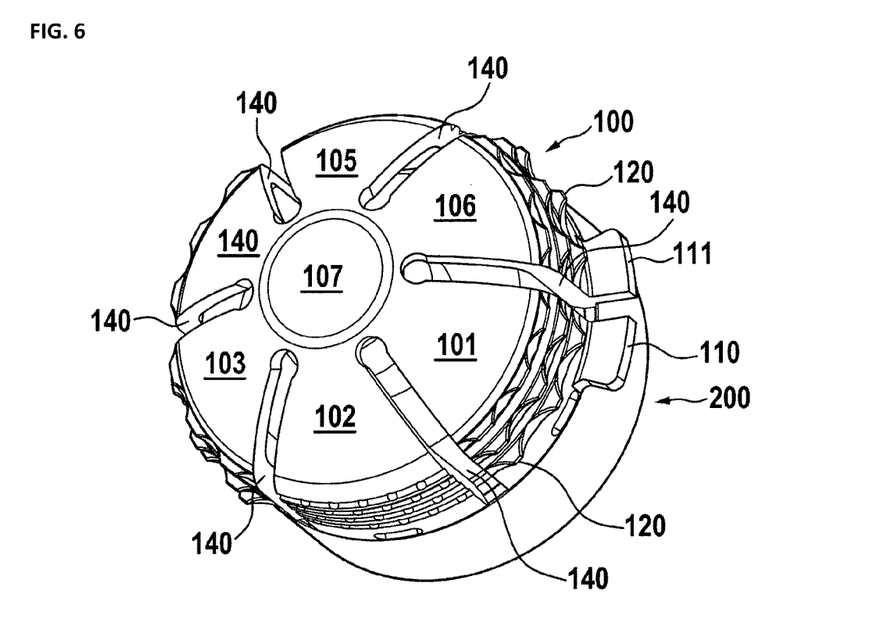
FIG. 6 shows a perspective view to the bottom side.

FIG. 6 shows a perspective view to the bottom side. Here, the sidewall segments are numbered from 101 to 106.

Figure 7:
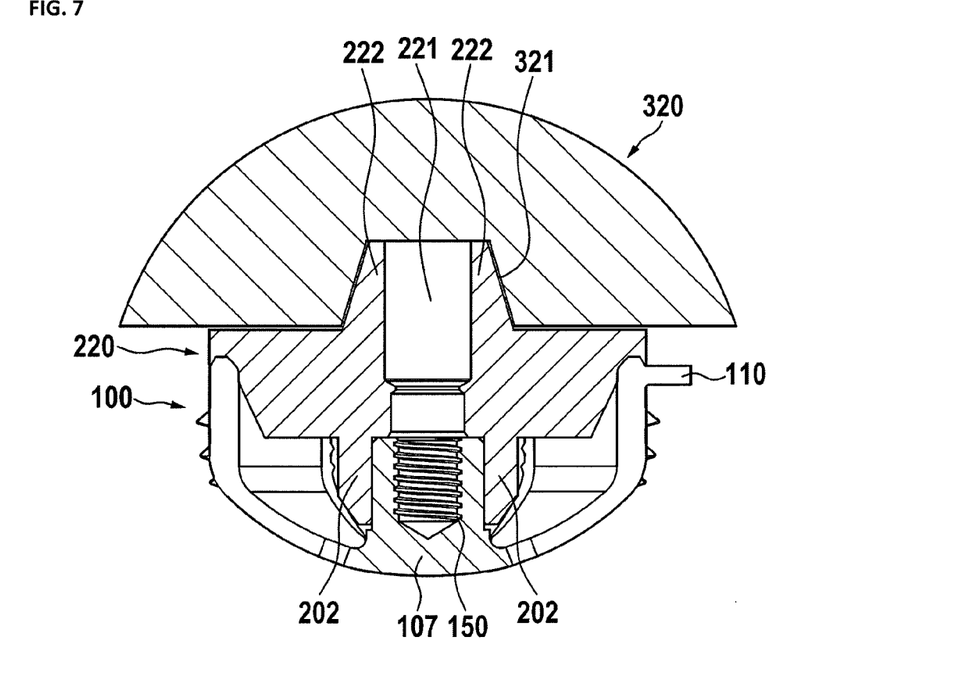
FIG. 7 shows an embodiment with a spherical cap.

FIG. 7 shows a spherical cap 320 positioned on a locking adapter 220.

Here, the locking adapter has a tapered shank 222, which fits into a conical hole 321 of the spherical cap 320.

Figure 8:
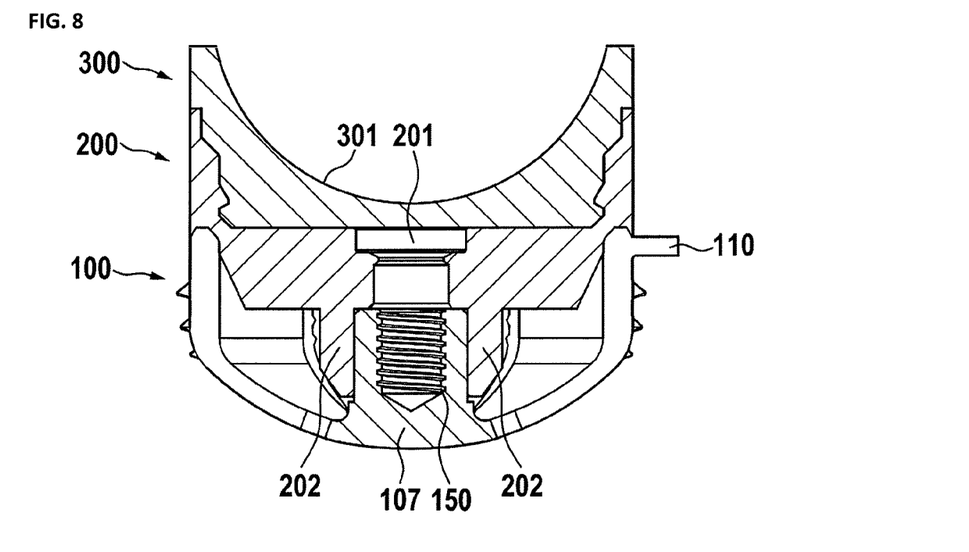
FIG. 8 shows an embodiment with a spherical liner.

FIG. 8 shows a humerus component 300 of a reverse prosthesis mounted into the locking adapter to 200 in cross sectional view. It has a preferably spherical inner surface 301.

Figure 9:
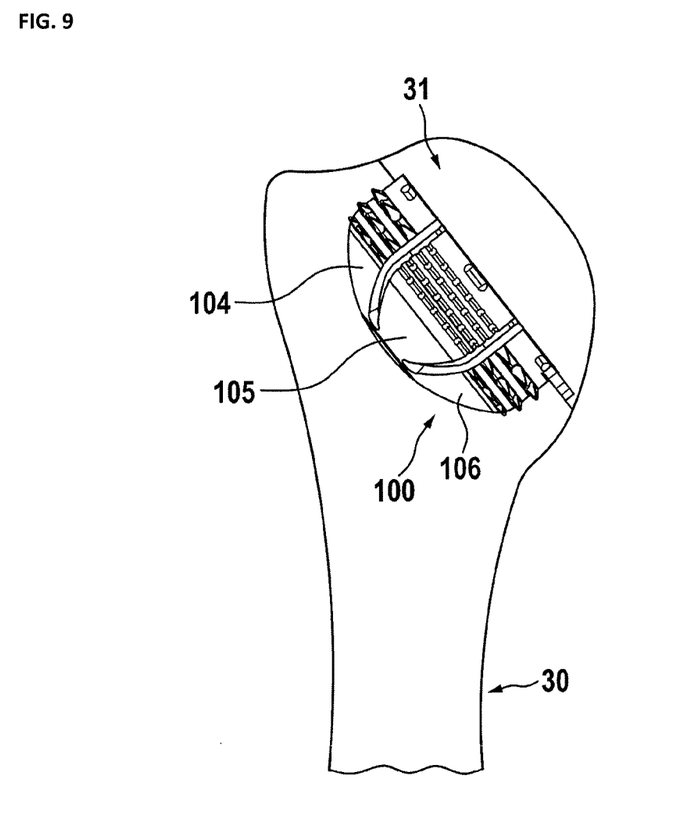
FIG. 9 shows a humerus with an inserted implant.

FIG. 9 shows a humerus 30 with an inserted implant 100 in the cancellous bone. Before insertion of the implant, the top section (31) of the humerus head has to be resected and an excavation for the body must be made. The optimum position of the implant can be selected by the position and angle under which the top section 31 of the humerus is cut away.

Figure 10:
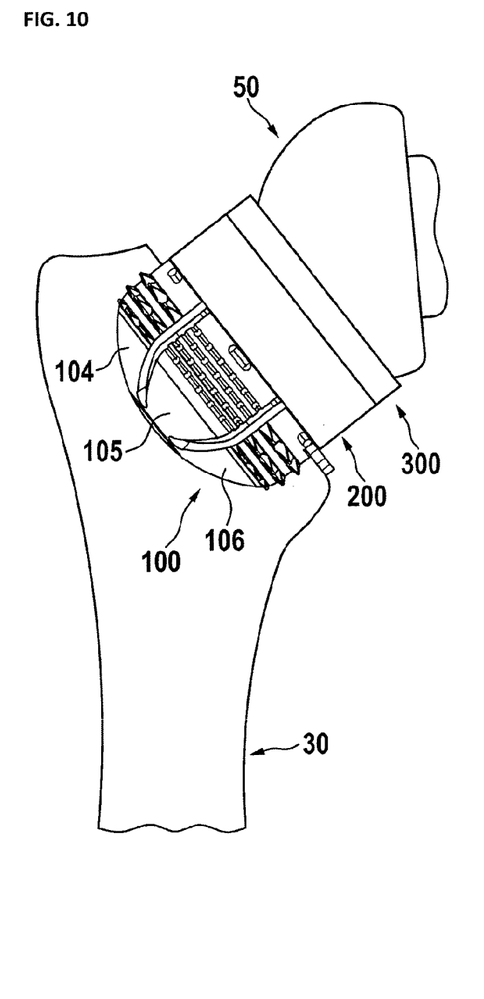
FIG. 10 shows a glenoid component at the implant body.

FIG. 10 shows a spherical liner 300 interfacing a glenoid component 50 of a reverse shoulder prosthesis (also referred as inverse shoulder prosthesis). The implant is held within a humerus 30.

Figure 11:
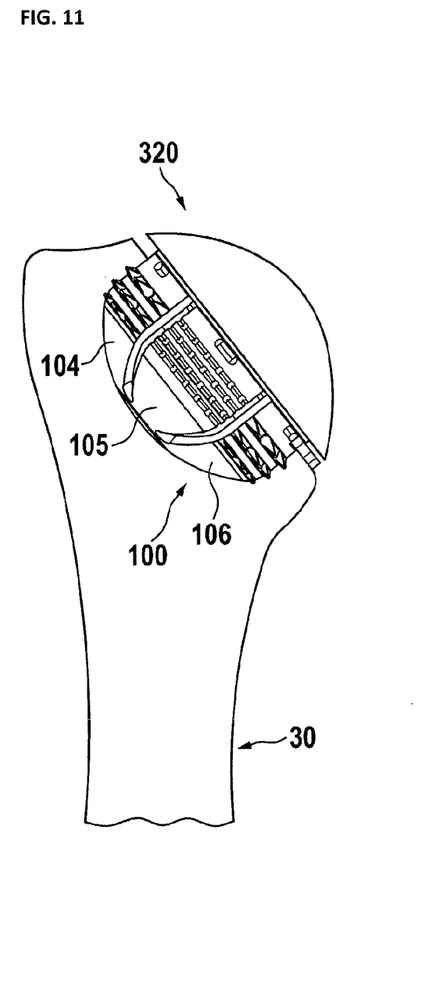
FIG. 11 shows a humerus component at the implant body.

FIG. 11 shows a humerus component 320 of an anatomical prosthesis mounted into a humerus 30.

Figure 12:
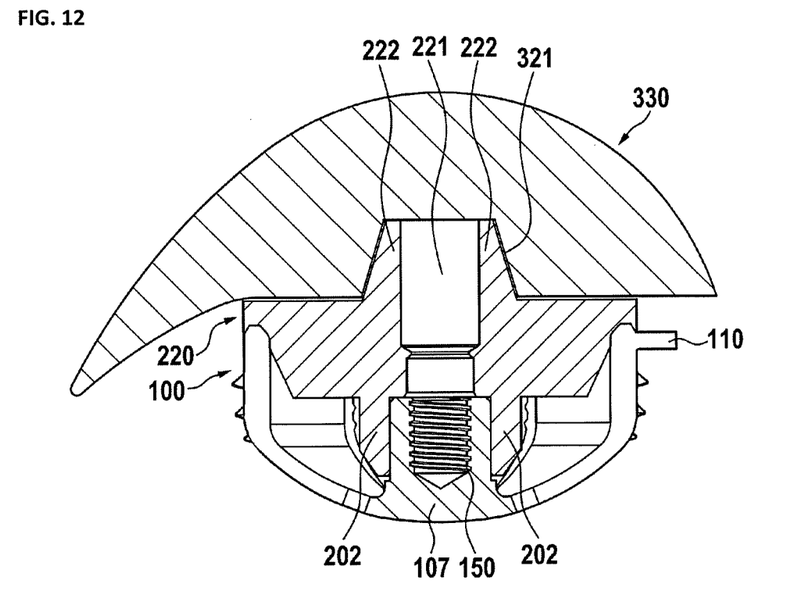
FIG. 12 shows a humerus component adapted to anatomical requirements.
Figure 13:
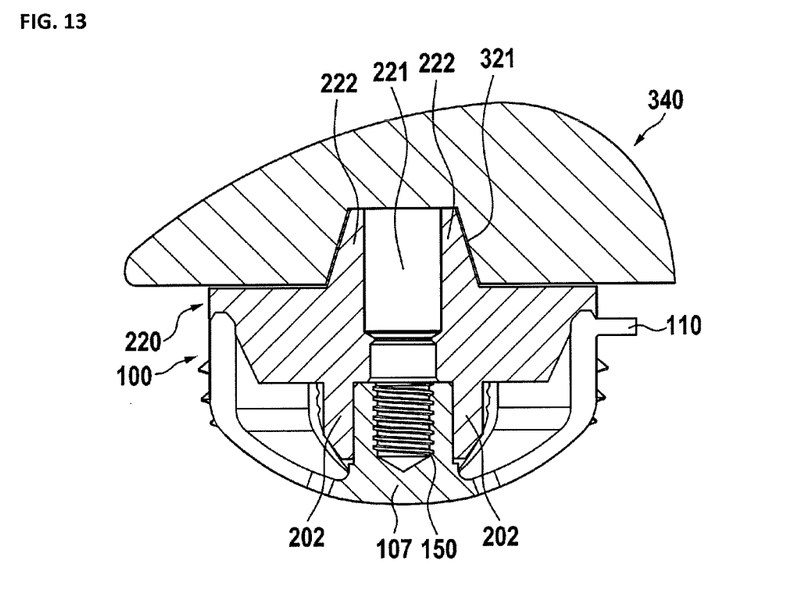
FIG. 13 shows another humerus component adapted to anatomical requirements.

FIGS. 12 and 13 show different embodiments of a humerus component 330, 340 of an anatomical prosthesis mounted into the implant body in cross sectional view. The humerus component is adapted to anatomical requirements.

It will be appreciated to those skilled in the art having the benefit of this disclosure that this invention is believed to provide a stemless reverse shoulder implant. Further modifications and alternative embodiments of various aspects of the invention will be apparent to those skilled in the art in view of this description. Accordingly, this description is to be construed as illustrative only and is for the purpose of teaching those skilled in the art the general manner of carrying out the invention. It is to be understood that the forms of the invention shown and described herein are to be taken as the presently preferred embodiments. Elements and materials may be substituted for those illustrated and described herein, parts and processes may be reversed, and certain features of the invention may be utilized independently, all as would be apparent to one skilled in the art after having the benefit of this description of the invention. Changes may be made in the elements described herein without departing from the spirit and scope of the invention as described in the following claims.

LIST OF REFERENCE NUMERALS 30 humerus
31 resected portion of humerus head
50 glenoid component of a reverse shoulder prosthesis
100 cup shaped body
101-106 side wall segments
107 center portion
110, 111 tabs
120 first sidewall segments
121 gaps
122 locking fins
130 second sidewall segments
131 recesses
132 holes
140 gaps
150 threaded hole
200 looking adapter
201 hole for screw
202 centering means
203 means for holding further components
204 conical contour
205 locking ring
210 hole for screw 220 second locking adapter
221 hole for screw
222 tapered shank
300 humerus component of inverse prosthesis
301 spherical surface
320 spherical cap
321 conical hole
330 second cap
340 third cap

The invention claimed is:

1. A stemless humerus implant including a cup shaped body and a locking adapter, said cup shaped body including a center portion and a plurality of flexible first and second sidewall segments, with gaps between neighbored sidewall segments, said first sidewall segments including a plurality of locking fins, said second sidewall segments including a plurality of recesses and holes, said locking adapter including means for fixing the locking adapter to said cup shaped body and further including a locking ring for locking said sidewall segments into theft final positions, wherein said locking adapter is located partially internal to the cup shaped body and is provided with a hole that allows a screw to be inserted into the hole and to lock the locking adapter against the cup shaped body, wherein both the screw and the hole extend into the cup shaped body, wherein said locking ring has a groove oriented towards the flexible first and second sidewall segments, wherein the groove has an edge supporting the flexible first and second sidewall segments from the outside and surrounds edges of the flexible first and second sidewall segments to hold them firmly in their position independent of pushing or pulling forces, wherein said cup shaped body is adapted to be positioned directly into humerus and without a stem.

2. The humerus implant of claim 1, wherein at least one of said sidewall segments has at least one tab extending radially from said cup shaped body.

3. The humerus implant of claim 1, wherein four first sidewall segments and two second sidewall segments are provided.

4. The humerus implant of claim 1, wherein said locking adapter includes means for attaching a humerus component of an inverse prosthesis or means for attaching a spherical cap.

5. The humerus implant of claim 1, wherein said locking adapter includes a tapered shank for attaching a further component.

6. The humerus implant of claim 1, wherein said locking adapter includes a conical outer contour at which said sidewall segments can slide during insertion of the locking adapter into said cup shaped body and are adapted to be pressed outwards towards the bone.

7. A stemless humerus implant including a cup shaped body and a locking adapter, said cup shaped body including a threaded center portion and a plurality of flexible sidewall segments, with gaps between neighbored sidewall segments, said locking adapter including a screw for fixing the locking adapter to said cup shaped body and further including a locking ring for locking said sidewall segments into their final positions, wherein said locking adapter is located partially internal to the cup shaped body and is provided with a hole that allows a screw to be inserted into the hole and to lock the locking adapter against the cup shaped body, wherein both the screw and the hole extend into the cup shaped body, wherein said threaded center portion extends into a space surrounded by the plurality of flexible sidewall segments, wherein said locking ring has a groove oriented towards the flexible first and second sidewall segments, wherein the groove has an edge supporting the flexible first and second sidewall segments from the outside and surrounds edges of the flexible first and second sidewall segments to hold them firmly in their position independent of pushing or pulling forces.

8. The humerus implant of claim 7, wherein first sidewall segments including a plurality of locking fins are provided.

9. The humerus implant of claim 7, wherein second sidewall segments including a plurality of recesses and holes are provided.

10. The humerus implant of claim 7, wherein at least one of said sidewall segments has at least one tab extending radially from said cup shaped body.

11. The humerus implant of claim 7, wherein four first sidewall segments and two second sidewall segments are provided.

12. The humerus implant of claim 7, wherein said locking adapter includes means for attaching a humerus component of an inverse prosthesis or means for attaching a spherical cap.

13. The humerus implant of claim 7, wherein said locking adapter includes a tapered shank for attaching a further component.

14. The humerus implant of claim 7, wherein said locking adapter includes a conical outer contour at which said sidewall segments can slide during insertion of the locking adapter into said cup shaped body and are adapted to be pressed outwards towards the bone.

* * * * *